United States Patent [19]

Muchowski et al.

[11] Patent Number: 4,755,531

[45] Date of Patent: Jul. 5, 1988

[54] THIOL ESTERS OF 4,5-ALLENYL PROSTAGLANDINS AND USE THEREOF AS ANTIGASTRIC SECRETION AGENTS

[75] Inventors: Joseph M. Muchowski, Sunnyvale, Calif.; Angel Guzman, Mexico City, Mexico

[73] Assignee: Syntex (U.S.A.) Inc., Palo Alto, Calif.

[21] Appl. No.: 895,067

[22] Filed: Aug. 11, 1986

[51] Int. Cl.$^4$ ............... C07C 153/023; A61K 31/265
[52] U.S. Cl. ................................. 514/513; 558/257
[58] Field of Search ..................... 558/257; 514/513

[56] References Cited

U.S. PATENT DOCUMENTS

| | | | |
|---|---|---|---|
| 3,833,635 | 9/1974 | Henrick | 558/257 |
| 3,985,791 | 10/1976 | Muchowski et al. | 558/257 |
| 4,096,178 | 6/1978 | Nelson | 560/53 |
| 4,147,877 | 4/1979 | Smith | 560/53 |
| 4,178,457 | 12/1979 | Van Horn et al. | 560/53 |
| 4,223,157 | 9/1980 | Axen | 560/53 |
| 4,249,001 | 2/1981 | Wenger | 558/257 |
| 4,278,688 | 7/1981 | Hayashi et al. | 560/53 |
| 4,600,785 | 7/1986 | Cooper et al. | 549/212 |

FOREIGN PATENT DOCUMENTS 2803058  7/1979  Fed. Rep. of Germany ...... 558/257

OTHER PUBLICATIONS

S. Masamune et al., Can. J. Chem., 53, 3693–5 (1975), "A General, Selective Synthesis of Thiol Esters".

*Primary Examiner*—Alan L. Rotman
*Assistant Examiner*—Robert C. Whittenbaugh
*Attorney, Agent, or Firm*—Derek P. Freyberg; Tom M. Moran

[57] ABSTRACT

Thiol esters of 4,5-allenyl prostaglandins, methods of making them, and pharmaceutical compositions containing them. These compounds are useful as gastric acid secretion inhibitors.

11 Claims, No Drawings

THIOL ESTERS OF 4,5-ALLENYL PROSTAGLANDINS AND USE THEREOF AS ANTIGASTRIC SECRETION AGENTS

BACKGROUND OF THE INVENTION

1. Field of the Invention

This invention relates to novel prostaglandins, particularly to novel thiol esters of 4,5-allenyl prostaglandins, their method of manufacture, their use in pharmaceutical compositions, and their use in treating gastrointestinal disorders.

2. Relevant Art

Enprostil is disclosed in U.S. Pat. No. 4,178,457, issued to Van Horn, which is hereby incorporated, in full, by reference. The thiol ester of enprostil is not disclosed therein.

Fenprostalene is disclosed in U.S. Pat. No. 3,985,791, issued to Muchowski, which is hereby incorporated, in full, by reference. The thiol ester of fenprostalene is not disclosed therein.

Thiol esters of prostaglandins are disclosed, for example, in U.S. Pat. No. 4,249,001. Thiol ester disclosures are unusual in the prostaglandin art.

The use of thallium (I) thioalkylate salts to form thiol esters of organic acids is disclosed in S. Masamune et al, *J. Canadian Chem.*, 53, 3692, (1975).

SUMMARY OF THE INVENTION

An aspect of this invention is a compound having the structure represented by the formula:

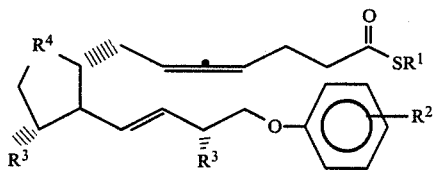

where:

$R^1$ is alkyl, cycloalkyl, aryl, or aralkyl;

$R^2$ is hydrogen, halo, trifluoromethyl, lower alkyl, lower alkoxy;

each $R^3$ is independently hydroxy, or protected hydroxy; and $R^4$ is C(O) or CH($R^3$), where $R^3$ is independently defined above.

A further aspect of this invention is a method of treating a mammal having a gastrointestinal disease state characterized by the over secretion of gastric acid which method comprises administering a therapeutically effective amount of a compound of formula (A), where $R^4$ is C(O), to the mammal.

A further aspect of this invention is a pharmaceutical formulation which comprises a compound of formula (A), where $R^4$ is C(O), and a pharmaceutically acceptable excipient.

This invention also provides methods of making compounds having the formula (A) as hereinafter described.

DETAILED DESCRIPTION OF THE INVENTION

Definitions

As used herein all prostaglandins will be named and numbered as derivatives of prostanoic acid. Prostanoic acid has the structure and numbering as shown below:

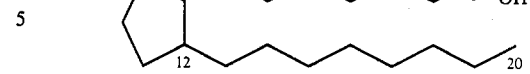

As understood in the art naturally occurring prostaglandins have the stereochemistry defined by 8-α,12-β substituents on the cyclopentyl ring. Mixtures of natural (8-α,12-β) and unnatural (8-β,12-α) configurations of prostanoic acid derivatives will be designated D,L. In this specification the drawings will depict the prostaglandins of this invention in the natural configuration, but it is understood that such depiction in the claims or specification encompasses each individual optical isomer, and mixtures thereof, whether racemic or not.

Certain novel compounds of the present invention are related in structure to E-type prostaglandins. E-type prostaglandins have a ketone functionality at the 9 position of prostanoic acid and are further characterized by 11-α and 15-α hydroxyl groups.

Certain other novel compounds of the present invention are related in structure to F-type prostaglandins. F-type prostaglandins have a 9-α hydroxyl and are further characterized by 11-α and 15-α hydroxyl groups.

When geometric isomers are possible at the double bond at 13,14 only the trans isomer falls within the scope of the claims.

As used herein the 8(R) isomer of a compound of formula (A) means the isomer defined by 8-α,12-β, 11-α hydroxyl, and 15-α hydroxyl or, equivalently, the natural configuration.

It is understood in the art that allenes have optical isomerism. All preferred isomers will be specifically designated (R) or (S). A brief discussion of the (R)-(S) formalism is found at *Organic Chemistry, Third Edition*, J. B. Hendrickson, D. J. Cram, and G. S. Hammond, McGraw-Hill, 1970, p 204–205.

Fenprostalene is the United Stated Adopted Name for methyl-9α,11α,15α-trihydroxy-16-phenoxy-17,18,19,20-tetranorprosta-4,5,13-trans-trienoate, and has the structure:

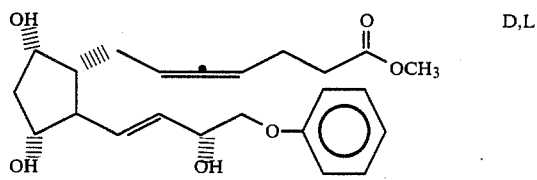

Enprostil is the United States Adopted Name for methyl-11α,15α-dihydroxy-9-oxo-16-phenoxy-17,18,19,20-tetranorprosta-4,5,13-trans-trienoate, and has the structure:

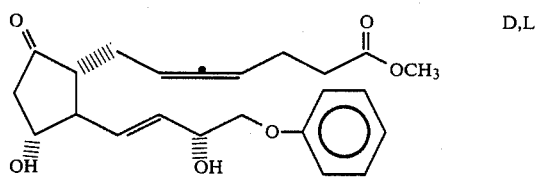

One obtains stereospecific isomers of fenprostalene and enprostil thiol esters by the method of U.S. Pat. No. 4,600,785, which is hereby incorporated by reference. The protected 4,5,6-(R) allenic fenprostalene, identified as compound 14 in that case, is deprotected. This compound is then used as the starting material for making the 4,5,6-(R) allenic isomer of enprostil.

The prostaglandins of this invention all have a 4,5 allenyl funtionality.

As used herein the terms "alkyl" means a branched, unbranched or cyclic saturated hydrocarbon chain radical having up to 20 carbon atoms. Examples include methyl, ethyl, propyl, isopropyl, cyclopropyl, t-butyl, 1,1-dimethylpropyl, n-hexyl, cyclohexyl, octyl, 1,1-diethylhexyl, dodecyl, hexadecyl, 1,1-dimethylhexadecyl, eicosyl and the like.

As used herein the term "hindered alkyl" means those alkyl groups, as defined above, represented by the formula $-C(R^4)(R^5)(R^6)$ where $R^4$ can be hydrgen or alkyl, and $R^5$ and $R^6$ are independently alkyl. $R^5$ and $R^6$ can be joined thereby forming a saturated hydrocarbon ring having from three to eight members. The hindered alkyl groups of this invention include those with secondary or tertiary carbon atoms as the bonding atom. Examples include isopropyl, cyclopropyl, t-butyl, 1,1-dimethylpropyl, cyclohexyl, 1,1-diethylhexyl, and 1,1-dimethylhexadecyl.

As used herein the term "alkoxy" means the radical —OR wherein R is alkyl as defined above. Examples include methoxy, ethoxy, propoxy, 2-propoxy, cyclopropoxy, t-butoxy, 1,1-dimethylpropyloxy, n-hexyloxy, cyclohexyloxy, octyloxy, 1,1-diethylhexyloxy, dodecyloxy, hexadecyloxy, 1,1-dimethylhexadecyloxy, eicosyloxy and the like.

As used herein the term "lower" as used herein, modifies alkyl, and alkoxy, and refers to those radicals having two carbon atoms or less.

As used in herein the term "cycloalkyl" means saturated hydrocarbon radicals that form a ring and have from three to six carbon atoms, for example, cyclopropane, cyclobutane, cyclopentane, and cyclohexane.

As used herein the term "optional" or "optionally" means that the subsequently described event or circumstance may or may not occur, and that the description includes instances where said event or circumstance occurs and instances in which it does not.

As used herein the term "optionally substituted phenyl" means that the phenyl may or may not be substituted, including both unsubstituted phenyl and phenyl wherein there is substitution. As used herein phenyl groups may be substituted with halo, alkyl, alkoxy, or trifluoromethyl.

As used herein the term "aryl" means optionally substituted phenyl or naphthyl.

As used herein the term "aralkyl" means a radical having an aryl radical substituted onto an alkyl radical. Examples include benzyl and 2-phenylethyl.

As used herein the term "protected hydroxy" means the oxygen of the alchohol is bonded to a removable group, that when chemically removed restores the hydroxy group. Preferred compounds for forming protected hydroxys include those formed from tetrahydropyranyl, tetrahydrofuranyl, dimethyl-t-butylsilyl, and the like.

As used herein the term "halo" means fluoro, chloro, bromo, and iodo.

The term "treatment" as used herein covers any treatment of a disease in a mammal, and includes:

(i) preventing the disease, that is, causing the clinical symptoms of the disease not to develop;

(ii) inhibiting the disease, that is, arresting the development of clinical symptoms; or (iii) relieving the disease, that is, causing regression of clinical symptoms.

Preferred Embodiments of the Invention

One preferred group of compounds of this invention is represented by formula A where $R^2$ is hydrogen and $R^3$ is hydroxy or protected hydroxy. A preferred subgroup includes those compounds where $R^1$ is lower alkyl or benzyl. Another preferred subgroup includes those compounds where $R^1$ is a hindered alkyl, especially where $R^1$ is cycloalkyl.

UTILITY AND METHODS OF ADMINISTRATION

The compounds of this invention are useful for treating a variety of disease states. It is known that allenyl containing E-type prostaglandins are useful in treating gastrointestinal disorders relating to over secretion of gastric acid. The compounds of this invention are similarly useful. Disease states that may be treated include ulcers, and spastic colon syndrome.

Generally, the gastrointestinal diseases are found in mammals including domestic commercial animals such as horses, cattle, sheep and pigs; domestic house animals such as dogs, cats and the like; and particularly humans.

The efficacy of the compounds of this invention can be determined using the standard Shay test for acid secretion in rats.

The compounds of this invention are administered at a therapeutically effective dosage, i.e. a dosage sufficient to relieve the gastrointestinal symptoms. Administration of the active compounds and salts described herein can be via any of the accepted modes of administration for prostaglandins. Depending on the specific disease state, adminstration can be systemic, via parenteral, oral, intravenous, nasal routes, or topical. In general the oral route of adminstration is preferred although other routes may be preferred for a specific disease state.

Prostaglandins are known to be difficult to formulate. One approach that is known to work for many E-type prostaglandins is dissolving the prostaglandin in an inert organic solvent, for example, propylene carbonate, and placing the formulation in a soft gelatin capsule. Liquid pharmaceutically administerable compositions can, for example, be prepared by dissolving, dispersing, and the like, compound of formula (A) as defined above and optional pharmaceutical adjuvants in a carrier, such as, for example, propylene glycol, propylene carbonate, glycerol, ethanol, and the like, to thereby form a solution or suspension. The formulated prostaglandin can then be orally ingested.

See U.S. Pat. No. 4,328,245 for a description of how to formulate prostaglandins in propylene carbonate solution and U.S. Pat. No. 4,409,239 for a description of how to formulate prostaglandins in a propylene glycol solution. Other formulations for prostaglandins are found in U.S. Pat. Nos. 3,749,800 dissolved in ethanol; 3,966,962 dissolved in dimethyl acetamide; 4,211,793 triethyl citrate; 3,826,832 lyophilizing with polyvinylpyrrolone; 4,301,146 lyophilizing with hydroxymethyl cellulose; and 4,054,736 lyophilizing with cyclodextrins. The disclosures of these Patents are hereby incorporated by reference.

The formulation of this invention can contain from 0.001 weight percent (wt. %) to 10.0 wt. % of compound of formula (A) and from 99.999 wt. % to 90.0 wt. % inert excipients.

The active compound as defined above may be formulated as suppositories using, for example, polyalkylene glycols, for example, propylene glycol, as the carrier. For systemic administration via suppository, traditional binders and carriers include, e.g. polyalkalene glycols or triglycerides. Such suppositories may be formed from mixtures containing the active ingredient in the range of 0.005 wt. %–10 wt. %; preferably 0.01–0.02 wt. %.

If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see, *Remington's Pharmaceutical Sciences,* Mack Publishing Company, Easton, Pa., 18th Edition, 1975. The composition or formulation to be administered will, in any event, contain a quantity of the active compound(s) in an amount effective to alleviate the symptoms of the subject being treated.

For oral administration, a pharmaceutically acceptable nontoxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 0.001 weight percent (wt. %) to 10.0 wt. % of compound of formula (A) and from 99.999 wt. % to 90.0 wt. % inert excipients, preferably 0.025–0.070 wt. % active ingredient.

METHODS OF PREPARATION

The compounds of this invention can be prepared by the method presented in schematic form below in REACTION SCHEME I.

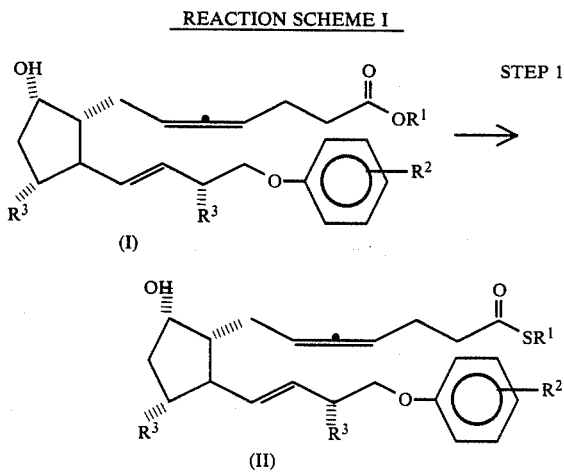

-continued
REACTION SCHEME I

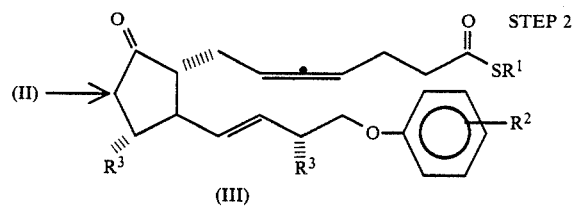

where $R^1$, $R^2$, and $R^3$ are as defined in the Summary of the Invention above.

The compounds of this invention are made by reacting a suitable F-type prostaglandin with thallium (I) thiolate salt. The corresponding E-type prostaglandin is made by the method of Yankee and Fried (*J. Chem. Soc., Chem. Comm.,* (1972), p 1120). In that method, the F-type prostaglandin is selectively protected and then reacted with Collins reagent.

In STEP 1 compound (I), the F-type prostaglandin, which can be fenprostalene when $R^1$ is hydrogen $R^2$ is hydrogen and $R^3$ is hydroxyl, is dissolved in an inert organic solvent, for example ethyl ether or tetrahydrofuran. A solution of an organic base, for example, triethylamine, is added followed by the slow addition of diethylphosphorochloridate. After stirring for between one and eight hours, preferably about three hours, the hydrochloride formed from the organic base is removed by filtration. Then a solution of the thallium (I) thioalkylate salts, for example, thallium benzylthiolate, is added. Examples of suitable thallium salts include thallium (I) methylthiolate, thallium (I) ethylthiolate, thallium (I) t-butylthiolate, thallium (I) hexylthiolate, thallium (I) phenylthiolate, and the like. These thallium (I) thiolate salts can be made by Masamune's procedure starting with mercaptans prepared from the corresponding alkyl halide and thiourea followed by alkyline hydrolysis of the intermediate isothiouronium salts. See L. G. Faehl et al, *J. Org. Chem.,* 45, 5207 (1980) and H. J. Baker, *Rec. Trav. Chim.,* 54, 216 (1935). The thiol ester is then isolated by conventional techniques and (II) is isolated.

In STEP 2, the corresponding E-type prostaglandin compound (III) is obtained by selectively protecting the 11 and 15 hydroxyl groups of the F-type prostaglandin, compound (II). A sterically hindered protecting agent, for example, N,N-diethyltrimethylsilylamine, is added to a solution of compound (II). The silylating agent should have enough steric hindrance to silylate only the 11 and 15 hydroxyl groups.

The thiol ester (II) is oxidized to the ketone (III) with chromium trioxide, preferably in the presence of pyridine, and particularly in form of Collins Reagent $((C_5H_5N)_2Cr(VI)O_3)$. Collins reagent is preferably suspended in a chlorinated hydrocarbon solvent, preferably dichloromethane. The oxidation continues for between about 5 to 60 minutes, preferably about 15 minutes, then the reaction is quenched, with, for example, ethyl acetate, and the compound of formula (III) purified by conventional chromatographic techniques.

The protecting groups can be removed by conventional techniques, for example, in the case of trimethylsilyl the protecting group is removed by contacting (III) with an aqueous solution of ethanol.

Compounds of the formula (A) having the 4,5,6-(R) allenic stereochemistry can be obtained by the method of U.S. Pat. No. 4,600,785, incorporated by reference. The protected 4,5,6-(R) allenic compounds of the formula (A) made by the method of Example 18 in that application and identified as compound 14 in that application, is deprotected. The compound is then used as the starting material of formula (I) for the synthesis above.

SUMMARY OF METHODS OF PREPARATION

The compounds of formula (A) can be produced by reacting compounds of formula (I) with the appropriate thallium (I) thiolate salt. The corresponding compounds of formula (II) can be made by selectively protecting the hydroxy groups on fenprostalene and oxidizing the resulting compound with Collins reagent.

EXAMPLES

EXAMPLE 1

Benzyl-9α,11α,15α-trihydroxy-16-phenoxy-17,18,19,20-tetranorprosta-4,5,13-trans-trienthiolate otherwise known as fenprostalene benzylthiol ester A. Four hundred fifty six mg (1.17 mmoles) of 9α,11α,15α-trihydroxy-16-phenoxy-17,18,19,20-tetranorprosta-4,5,13-trans-trienoic acid were dissolved, under an atmosphere of argon, in 18 ml of anhydrous tetrahydrofuran. 0.36 ml (2.58 mmoles) of triethylamine was added to this solution, followed by the dropwise addition of 0.314 ml (2.58 mmoles) of diethylphosphorochloridate dissolved in 5 ml of anhydrous tetrahydrofuran. This reaction mixture was stirred at room temperature for three hours, then the triethylamine hydrochloride was removed by filtration and 1.05 g of thallium (I) benzylthiolate was added to the resulting solution. The reaction mixture thus obtained was stirred at room temperature for 18 hours, then the solvent was removed under reduced pressure, the residue was diluted with dichloromethane, and the solid which formed was removed by filtration. After the solvent was removed under reduced pressure, the filtrate gave benzyl-9α,11α,15α-trihydroxy-16-phenoxy-17,18,19,20-tetranorprosta-4,5,13-trans-trienthiolate, ir, (CHCl$_3$) 3590, 1960, 1685, 1600, 1590 cm$^{-1}$, which was purified by preparative thin layer chromatography (prep-TLC) on silica gel using ethyl acetate as the developing solvent.

B. Similarly, by following the procedure of Part A of the Example above, but replacing thallium (I) benzylthiolate with:
  thallium (I) ethylthiolate and
  thallium (I) methylthiolate,
one obtains:
  fenprostalene ethylthiol ester, ir, (CHCl$_3$) 3590, 3430, 1965, 1690, 1600, 1590 cm$^{-1}$, and
  fenprostalene methylthiol ester, ir, (CHCl$_3$) 3590, 3430, 1965, 1685, 1600, 1590 cm$^{-1}$.

C. Similarly, by following the procedure of Part A of the Example above, but replacing thallium (I) benzylthiolate with:
  thallium (I) t-butylthiolate and
  thallium (I) hexylthiolalte,
one obtains:
  fenprostalene t-butylthiol ester and
  fenprostalene hexylthiol ester.

D. Similarly, by following the procedure of Parts A, B, and C of the Example above, are replacing 9α,11α,15α-trihydroxy-16-phenoxy-17,18,19,20-tetranorprosta-4,5,13-trans-trienoic acid with:
  8(R)-9α,11α,15α-trihydroxy-16-phenoxy-17,18,19,20-tetranorprosta-4,5(R),13-trans-trienoate
one obtains:
  benzyl-8(R)-9α,11α,15α-trihydroxy-16-phenoxy-17,18,19,20-tetranorprosta-4,5(R),13-trans-trienethiolate;
  ethyl-8(R)-9α,11α,15α-trihydroxy-16-phenoxy-17,18,19,20-tetranorprosta-4,5(R),13-trans-trienethiolate;
  methyl-8(R)-9α,11α,15α-trihydroxy-16-phenoxy-17,18,19,20-tetranorprosta-4,5(R),13-trans-trienethiolate;
  t-butyl-8(R)-9α,11α,15α-trihydroxy-16-phenoxy-17,18,19,20-tetranorprosta-4,5(R),13-trans-trienethiolate; and
  hexyl-8(R)-9α,11α,15α-trihydroxy-16-phenoxy-17,18,19,20-tetranorprosta-4,5(R),13-trans-trienethiolate.

EXAMPLE 2

Benzyl-1α,15α-dihydroxy-9-oxo-16-phenoxy-17,18,19,20-tetranorprosta-4,5,13-trans-trienethiolate also known as enprostil benzylthiol ester.

A. Five ml (26.4 mmoles) of N,N-diethyltrimethylsilylamine was added, with agitation, to 383 mg (0.774 mmoles) of benzyl-9α,11α,15α-trihydroxy-16-phenoxy-17,18,19,20-tetranorprosta-4,5,13-trans-trienethiolate dissolved in 6 ml of dry acetone cooled to −30° C. under argon. The reaction mixture was stirred at −30° C. for 4.5 hours, and then 3.75 ml of anhydrous methanol and 50 ml of toluene was added thereto. The solvent was then removed under reduced pressure. The residue was then dissolved in 20 ml of dry dichloromethane and added to a suspension, at −10° C., of 4 grams of Celite, 2.07 grams, 7.74 mmoles) of Collins reagent and 25 ml of dichloromethane. This suspension was stirred at −10° C. for 20 minutes, then 50 ml of ethyl acetate was added, the solid removed by filtration and the solvent of the filtrate removed under reduced pressure. Five ml of ethanol:water (7:3) was added to the residue and the resulting material was left at room temperature for four hours. The solvent was removed under reduced pressure and benzyl-1α,15α-dihydroxy-9-oxo-16-phenoxy-17,18,19,20-tetranorprosta-4,5,13-trans-trienethiolate, ir, (CHCl$_3$) 3580, 3420, 1960, 1745, 1685, 1600, 1590 cm$^{-1}$, was purified by prep-TLC on silica gel using ethyl acetate hexane 7:3 as the developing solvent.

B. Similarly, by following the procedure of Part A of the Example above, but replacing benzyl-9α,11α,15α-trihydroxy-16-phenoxy-17,18,19,20-tetranorprosta-4,5,13-trans-trienethiolate with:
  fenprostalene ethylthiol ester and
  fenprostalene methylthiol ester
one obtains:
  enprostil ethylthiol ester, ir, (CHCl$_3$) 3580, 3430, 1965, 1745, 1685, 1600, 1590 cm$^{-1}$, and
  enprostil methylthiol ester, ir, (CHCl$_3$) 3590, 3420, 1965, 1745, 1685, 1600, 1590 cm$^{-1}$.

C. Similarly, by following the procedure of Part A of the Example above, but replacing benzyl-9α,11α,15α-trihydroxy-16-phenoxy-17,18,19,20-tetranorprosta-4,5,13-trans-trienethiolate with:
  fenprostalene t-butylthiol ester and
  fenprostalene hexylthiol ester
one obtains:
  enprostil t-butylthiol ester and
  enprostil hexylthiol ester can be made.

D. Similarly, by following the procedure of Part A of the Example above, but replacing benzyl-9α,11α,15α-trihydroxy-16-phenoxy-17,18,19,20-tetranorprosta-4,5,13-trans-trienethiolate with:

benzyl-8(R)-9α,11α,15α-trihydroxy-16-phenoxy-17,18,19,20-tetranorprosta-4,5(R),13-trans-trienethiolate;

ethyl-8(R)-9α,11α,15α-trihydroxy-16-phenoxy-17,18,19,20-tetranorporsta-4,5(R),13-trans-trienethiolate;

methyl-8(R)-9α,11α,15α-trihydroxy-16-phenoxy-17,18,19,20-tetranorprosta-4,5(R),13-trans-trienethiolate;

t-butyl-8(R)-9α,11α,15α-trihydroxy-16-phenoxy-17,18,19,20-tetranorprosta-4,5(R),13-trans-trienethiolate; and hexyl-8(R)-9α,11α,15α-trihydroxy-16-phenoxy-17,18,19,20-tetranorprosta-4,5(R),13-trans-trienethiolate, one obtains:

benzyl-8(R)-11α,15α-dihydroxy-9-oxo-16-phenoxy-17,18,19,20-tetranorprosta-4,5(R),13-trans-trienethiolate;

ethyl-8(R)-11α,15α-dihydroxy-9-oxo-16-phenoxy-17,18,19,20-tetranorprosta-4,5(R),13-trans-trienethiolate;

methyl-8(R)-11α,15α-dihydroxy-9-oxo-16-phenoxy-17,18,19,20-tetranorprosta-4,5(R),13-trans-trienethiolate;

t-butyl-8(R)-11α,15α-dihydroxy-9-oxo-16-phenoxy-17,18,19,20-tetranorprosta-4,5(R),13-trans-trienethiolate; and hexyl-8(R)-11α,15α-dihydroxy-9-oxo-16-phenoxy-17,18,19,20-tetranorprosta-4,5(R),13-trans-trienethiolate.

EXAMPLE 3

Formulation in Propylene Carbonate 1.0 Micrograms of enprostil benzyl ester was added to 10 ml of dry propylene carbonate. The mixture was then stirred with a blade type stirrer for an additional 15 minutes until a homogeneous solution was obtained. The solution was then encapsulated in soft gelatin capsules.

EXAMPLE 4

Determination of Gastric Juice Flow Inhibition
Materials and Methods

Hilltop, Sprague-Dawley derived male rats (200–250 g) were starved in individual cages for 48 hours prior to the experiment. A circular, plastic collar was stapled arount the neck of each rat to "prevent" coprophagy and hair ingestion. Water was available ad libitum. During the morning of the experiment, after 48 hours of starvation, the test compound was administered 30 minutes prior to surgery. The test compound was administered orally (p.o.). After compound administration, rats were anesthetized with ether, a ligature was placed and tied around the esophagus to prevent saliva from draining into the stomach. Midline laparotomy was performed to expose the stomach and a ligature was tied around the duodenum near the pyloric sphincter of the stomach. Incisions were then closed with wound clips and the animal injected with histamine, 40 mg/kg, subcutaneously once during the 3-hour experimental period. At the end of 3 hours, the rats were killed, gastric juice was completely aspirated from the stomach and volume recorded. An aliquot of this juice was titrated with 0.02 N sodium hydroxide to pH 7.0±0.1, using a Bechman pH meter to determine the end point. The milliequivalents of hydrogen chloride per 100 g of body weight were calculated. The pH was also recorded. Each dose of a test compouns was investigated in 8–10 rats. Statistical evaluation was done using Student's t-test.

What is claimed is:

1. A compound having the structure represented by the formula:

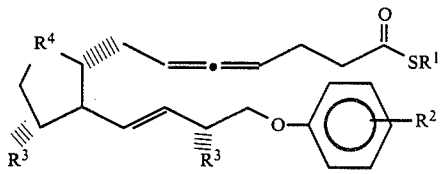

where:
$R^1$ is alkyl, cycloalkyl, aryl, or aralkyl;
$R^2$ is hydrogen, halo, trifluoromethyl, lower alkyl, or lower alkoxy;
each $R^3$ is independently hydroxy, or protected hydroxy; and
$R^4$ is C(O) or CH($R^3$), where $R^3$ is defined above, and where alkyl, cycloalkyl, aryl, and aralkyl are as defined in the specification.

2. The compound of claim 1 wherein $R^2$ is hydrogen, $R^4$ is CH($R^3$), and $R^3$ is hydroxy.

3. The compound of claim 2 wherein $R^1$ is benzyl, namely, benzyl 9α,11α,15α-trihydroxy-16-phenoxy-17,18,19,20-tetranorprosta-4,5,13-trans-trienethiolate.

4. The compound of claim 2 wherein $R^1$ is methyl, namely, methyl 9α,11α,15α-trihydroxy-16-phenoxy-17,18,19,20-tetranorprosta-4,5,13-trans-trienethiolate.

5. The compound of claim 2 wherein $R^1$ is ethyl, namely, ethyl 9α,11α,15α-trihydroxy-16-phenoxy-17,18,19,20-tetranorprosta-4,5,13-trans-trienethiolate.

6. The compound of claim 1 wherein $R^2$ is hydrogen, $R^4$ is C(O), and $R^3$ is hydroxy.

7. The compound of claim 2 wherein $R^1$ is benzyl, namely, benzyl-11α,15α-dihydroxy-9-oxo-16-phenoxy-17,18,19,20-tetranorprosta-4,5,13-trans-trienethiolate.

8. The compound of claim 2 wherein $R^1$ is methyl, namely, methyl 11α,15α-dihydroxy-9-oxo-16-phenoxy-17,18,19,20,-tetranorprosta-4,5,13-trans-trienethiolate.

9. The compound of claim 2 wherein $R^1$ is ethyl, namely, ethyl 11α,15α-dihydroxy-9-oxo-16-phenoxy-17,18,19,20-tetranorprosta-4,5,13-trans-trienethiolate.

10. A method of treating a mammal having a gastrointestinal disease state by the over secretion of gastric acid which method comprises administering a therapeutically effective amount of a compound of claim 6 to the mammal.

11. A pharmaceutical formulation for treating a mammal having a gastrointestinal disease state by the over secretion of gastric acid which comprises a therapeutically effective amount of a compound of claim 6 and a pharmaceutically acceptable excipient.

* * * * *